United States Patent
Garstka et al.

(10) Patent No.: US 9,072,885 B2
(45) Date of Patent: Jul. 7, 2015

(54) SYSTEMS FOR HYDRATING DEFIBRILLATION ELECTRODES

(71) Applicant: Covidien LP, Mansfield, MA (US)

(72) Inventors: Erick Garstka, Westfield, MA (US); Warren W Copp-Howland, Chicopee, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/628,063

(22) Filed: Sep. 27, 2012

(65) Prior Publication Data

US 2014/0088657 A1    Mar. 27, 2014

(51) Int. Cl.
*A61N 1/04*    (2006.01)
*A61N 1/39*    (2006.01)

(52) U.S. Cl.
CPC ............ *A61N 1/046* (2013.01); *A61N 1/0472* (2013.01); *A61N 1/39* (2013.01); *A61N 1/0496* (2013.01)

(58) Field of Classification Search
CPC ......... A61N 1/142; A61N 1/39; A61N 1/046; A61N 1/0472; A61N 1/3625; A61N 1/3968; A61N 1/0496
USPC .......................................... 607/5, 7, 153, 142
See application file for complete search history.

(56) References Cited

U.S. PATENT DOCUMENTS

| | | | |
|---|---|---|---|
| 4,779,630 A | 10/1988 | Scharnberg et al. | |
| 5,462,157 A | 10/1995 | Freeman et al. | |
| 5,645,527 A * | 7/1997 | Beck | 604/20 |
| 5,797,867 A * | 8/1998 | Guerrera et al. | 604/20 |
| 5,797,969 A | 8/1998 | Olson et al. | |
| 5,817,151 A | 10/1998 | Olson et al. | |
| 6,083,246 A | 7/2000 | Stendahl et al. | |
| 6,115,638 A | 9/2000 | Groenke | |
| 6,314,320 B1 | 11/2001 | Powers et al. | |
| 6,321,113 B1 | 11/2001 | Parker et al. | |
| 6,556,864 B1 | 4/2003 | Picardo et al. | |
| 6,564,105 B2 * | 5/2003 | Starkweather et al. | 607/60 |
| 6,662,046 B2 | 12/2003 | Hansen | |
| 6,662,056 B2 * | 12/2003 | Picardo et al. | 607/142 |
| 6,675,051 B2 | 1/2004 | Janae et al. | |

(Continued)

FOREIGN PATENT DOCUMENTS

WO    WO 2007/08442 A2    7/2007
WO    WO 2007/127266 A2    11/2007

OTHER PUBLICATIONS

"Lifesaving Products;" Laerdal Products Catalogue 2008-2009; Jan. 2008; 148 pages.

(Continued)

*Primary Examiner* — Niketa Patel
*Assistant Examiner* — William Levicky
(74) *Attorney, Agent, or Firm* — Lisa E. Winsor, Esq.

(57) ABSTRACT

According to an aspect of the present disclosure, an automated external defibrillator is configured to deliver one or both of electrical pulses and shocks to a heart of a patient during a cardiac emergency. The defibrillator includes a defibrillator electrode delivery system and a hydrating system. The defibrillator electrode delivery system includes a pair of defibrillation electrode pads. Each pad supports a hydrogel to facilitate the deliverance of one or both of electrical pulses and shocks to a patient. The hydrating system includes a fluid container that maintains a fluid that hydrates the hydrogel over a predetermined time period to prolong the effectiveness of the hydrogel.

14 Claims, 1 Drawing Sheet

(56) References Cited

U.S. PATENT DOCUMENTS

| | | |
|---|---|---|
| 6,872,080 B2 | 3/2005 | Pastrick et al. |
| 6,874,621 B2 | 4/2005 | Solosko et al. |
| 6,928,322 B2 | 8/2005 | Yerkovich et al. |
| 6,948,295 B2 | 9/2005 | Biggins |
| 6,965,799 B2 | 11/2005 | Nova et al. |
| 6,969,259 B2 | 11/2005 | Pastrick et al. |
| 7,069,074 B2 | 6/2006 | Covey et al. |
| 7,072,712 B2 | 7/2006 | Kroll et al. |
| 7,231,247 B2 | 6/2007 | Faller et al. |
| 7,236,823 B2 | 6/2007 | Herbert |
| RE40,365 E | 6/2008 | Kirchgeorg et al. |
| 7,453,354 B2 | 11/2008 | Reiter et al. |
| 7,457,662 B2 | 11/2008 | Nassif |
| 7,463,923 B2 | 12/2008 | Brewer et al. |
| 7,489,972 B2 | 2/2009 | Denney et al. |
| 7,792,577 B2 | 9/2010 | Hamilton et al. |
| 7,797,044 B2 | 9/2010 | Covey et al. |
| 8,428,751 B2 | 4/2013 | Copp-Howland et al. |
| 8,594,763 B1* | 11/2013 | Bibian et al. .................. 600/383 |
| 2002/0117408 A1* | 8/2002 | Solosko et al. ............... 206/210 |
| 2006/0058846 A1 | 3/2006 | Smirles et al. |
| 2007/0235555 A1* | 10/2007 | Helf et al. .................. 239/102.2 |
| 2007/0255382 A1* | 11/2007 | Meyer et al. .................. 607/142 |
| 2009/0227857 A1 | 9/2009 | Rowe et al. |
| 2009/0270709 A1 | 10/2009 | Copp et al. |
| 2009/0270710 A1 | 10/2009 | Copp et al. |
| 2009/0281585 A1 | 11/2009 | Katzman et al. |
| 2010/0072060 A1 | 3/2010 | Copp-Howland |
| 2011/0230925 A1* | 9/2011 | Copp-Howland et al. ........ 607/8 |
| 2013/0289689 A1 | 10/2013 | Copp-Howland et al. |

OTHER PUBLICATIONS

European Search Report; dated Jun. 8, 2011; for EP Pat, App. No. 11157002.4; 6 pages.
U.S. Appl. No. 12/886,926.
U.S. Appl. No. 13/850,323.
Response to Office Action dated Mar. 4, 2014 for U.S. Appl. No. 13/850,323, 5 pages.
Terminal Disclaimer filed on May 19, 2014 for U.S. Appl. No. 13/850,323, 2 pages.
Notice of Allowance dated Jun. 9, 2014 for U.S. Appl. No. 13/850,323 7 Pages.

* cited by examiner

SYSTEMS FOR HYDRATING DEFIBRILLATION ELECTRODES

BACKGROUND

1. Technical Description

The present disclosure relates to defibrillators and defibrillation electrodes and, more particularly, to systems and methods for hydrating defibrillation electrodes connected to a defibrillator prior to the electrodes being used on a patient.

2. Background of Related Art

In many instances, when an emergency situation arises at a public location remote from a medical facility, Automated External Defibrillators (AED's) may generally be available for use on the individual experiencing the medical emergency. An AED is a portable electronic device that automatically diagnoses the potentially life threatening cardiac arrhythmias of ventricular fibrillation and ventricular tachycardia in a patient, and is able to treat them through defibrillation, the application of electrical therapy which stops the arrhythmia, allowing the heart to reestablish an effective rhythm.

Like many other medical devices, AED's include electrodes that generally have a conductor portion that is often covered or coated in a conductive gel/hydrogel to enhance the ability of the electrode to adhere to a patient's skin. However, an AED may be stored for prolonged periods which may cause the conductive gel/hydrogel to become dry to the point where its effectiveness is altered or compromised. In this respect, when an AED is stored for long periods of time, the conductive gel/hydrogel may lose its ability to adhere to a patient or may demonstrate excessively high contact impedance which, if used on a patient, can result in the patient being burned.

Thus, a need exists for a system that prolongs the lifespan of the conductive gel/hydrogel used with defibrillation electrodes to minimize risks associated with AEDs that will be stored for long periods of time.

SUMMARY

According to one aspect, an automated external defibrillator is configured to deliver electrical pulses and/or shocks to a heart of a patient during a cardiac emergency. The defibrillator includes a defibrillator electrode delivery system and a hydrating system. The defibrillator may include a controller operatively coupled to one or both of the defibrillator electrode delivery system and the hydrating system.

The defibrillator electrode delivery system includes a pair of defibrillation electrode pads and an energy source. Each pad supports a hydrogel to facilitate the deliverance of electrical pulses and/or shocks to a patient. Each defibrillation electrode pad is electrically coupled to the energy source to selectively enable the deliverance of electrical pulses and/or shocks to a patient. One or both of the defibrillation electrode pads are fixedly electrically coupled to the energy source.

The hydrating system includes a fluid container. The fluid container maintains a fluid that hydrates the hydrogel over a predetermined time period to prolong the effectiveness of the hydrogel. The fluid may be water.

The hydrating system may include a mesh supported on the fluid container The mesh may define a plurality of micro pores. The pair of defibrillation electrode pads may be supported on the mesh.

The hydrating system may include a sprayer configured to spray one or both of the defibrillation electrode pads with the fluid. The sprayer may be configured to periodically spray one or both of the defibrillation electrode pads with the fluid. The hydrating system may include a plurality of sprayers. Each sprayer may be configured to spray one or both of the defibrillation electrode pads with the fluid.

According to another aspect, an automated external defibrillator is configured to deliver electrical pulses and/or shocks to a heart of a patient during a cardiac emergency. The defibrillator includes a housing, a pair of defibrillation electrode pads, and a hydrating system. A controller maybe supported by the housing that is operatively coupled to the hydrating system.

The housing supports an electrical connector, a battery, and high voltage circuitry.

The pair of defibrillation electrode pads are supported on the housing. Each defibrillation electrode pad supports a hydrogel and is pre-connected to the electrical connector of the housing so that each defibrillation electrode pad is in electrical communication with the battery and the high voltage circuitry.

The hydrating system includes a fluid container within the housing. The housing may include the fluid container. The fluid container maintains a fluid that hydrates the hydrogel to prolong the effectiveness of the hydrogel. The fluid may be water. The hydrating system may include a mesh supported on the fluid container. The mesh may be supported on the housing. The mesh is in fluid communication with the fluid container. The pair of defibrillation electrode pads may be supported on the mesh.

The hydrating system may include a sprayer configured to spray one or both of the defibrillation electrode pads with the fluid. The sprayer may be configured to periodically spray one or both of the defibrillation electrode pads with the fluid. The hydrating system may include a plurality of sprayers. Each sprayer maybe configured to spray one or both of the defibrillation electrode pads with the fluid.

According to yet another aspect, a method of preserving a defibrillation electrode pad of an automated external defibrillator involves the step of providing an automated external defibrillator including a defibrillation pad and a hydrating system where the defibrillation pad supports a hydrogel. The method includes hydrating the hydrogel of the defibrillation pad with the hydrating system of the automated external defibrillator while storing the automated external defibrillator.

BRIEF DESCRIPTION OF THE DRAWINGS

Various embodiments of the presently disclosed systems are described herein with reference to the drawings wherein.

DETAILED DESCRIPTION

Figure 1:
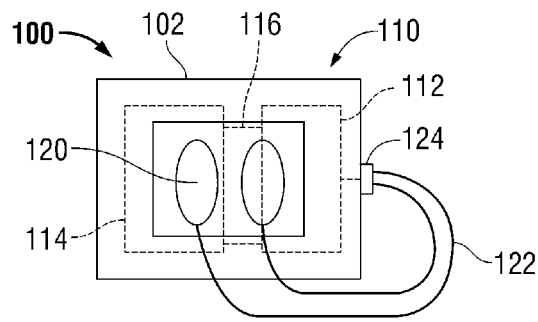
FIG. 1 is a top, plan schematic view of an exemplary automated external defibrillator.

Embodiments of the presently disclosed automated external defibrillators will now be described in detail with reference to the drawing figures wherein like reference numerals identify similar or identical elements.

As illustrated in FIG. 1, an exemplary automated external defibrillator is generally designated as 100. Automated external defibrillator 100 is configured to deliver electrical pulses and/or shocks to a heart of a patient during a cardiac emergency. Automated external defibrillator 100 includes a housing 102 and an electrode delivery system 110 supported by housing 102. Electrode delivery system 110 is configured to generate and deliver electrical pulses and/or shocks (e.g., manually and/or autonomously as appreciated by one skilled in the art). Electrode delivery system 110 includes a controller 112, an energy source 114 (e.g., a battery), and circuitry 116 in electrical communication with controller 112 and energy source 114. Circuitry 116 may be configured for high voltage compatibility. Notably, any suitable combination of conductors, resistors, transistors, capacitors, inductors, etc. may be used to electrically couple any of the presently disclosed components described herein.

With continuing reference to FIG. 1, electrode delivery system 110 includes a pair of electrode pads 120 that are electrically coupled to controller 112 and/or energy source 114 via lead wires 122 and an electrical connector 124 supported on or in electrical communication with a first end of lead wires 122. In this regard, electrical connector 124 electrically couples lead wires 122 and circuitry 116 to electrically couple controller 112 and/or energy source 114 to electrode pads 120 to deliver electrical pulses and/or shocks. The pair of electrode pads 120 are supported on or in electrical communication with a second end of lead wires 122.

Figure 2:
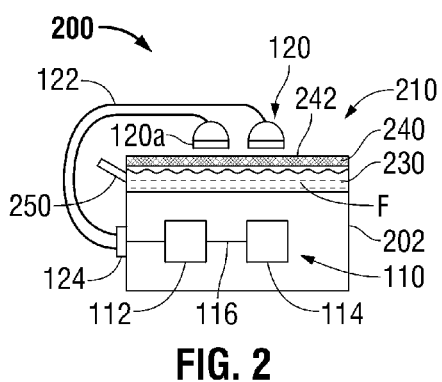
FIG. 2 is a side, elevational schematic view of an automated external defibrillator according to an embodiment of the present disclosure.
Figure 3:
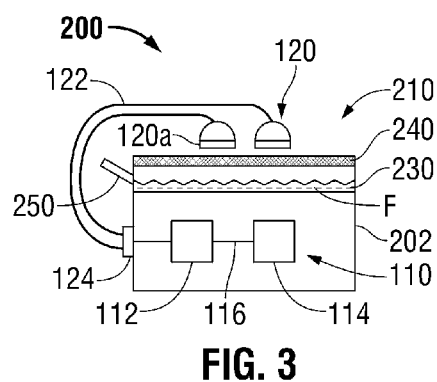
FIG. 3 is a side, elevational schematic view of the automated external defibrillator illustrated in FIG. 2, after a predetermined time period.

As illustrated in FIGS. 2-3, an automated external defibrillator according to one embodiment of the present disclosure is generally referred to as 200. Automated external defibrillator 200 is similar to automated external defibrillator 100 and is described herein only to the extent necessary to describe the differences in construction and operation thereof. Automated external defibrillator 200 includes a housing 202 that supports an electrode delivery system 110 and a hydrating system 210. Electrode pads 120 are pre-connected to controller 112 and/or energy source 114 such that electrode pads 120 are in electrical communication with controller 112 and/or energy source 114. Electrode pads 120 may be fixedly pre-connected to controller 112 and/or energy source 114. In order to facilitate the deliverance of electrical pulses and/or shocks to a patient, a hydrogel 120a (or other suitable material; e.g., a foam) is supported on electrode pads 120 of electrode delivery system 110. Hydrogel 120a enhances the ability of electrode pads 120 to adhere to a patient's skin when delivering electrical pulses and/or shocks generated by controller 112 and/or energy source 114.

With continuing reference to FIGS. 2-3, hydrating system 210 is configured to reduce a moisture vapor transmission rate (i.e., tendency to dry-out) of hydrogel 120a of electrode pads 120 without the need for special packaging of electrode pads 120. In this regard, electrode pads 120 may be pre-connected to controller 112 and/or energy source 114 to hasten the usability of electrode pads 120 by eliminating the need to open packaging and/or the need to electrically connect electrode pads 120 to controller 112 and/or energy source 114 at the time of a cardiac emergency.

As depicted in FIGS. 2-3, hydrating system 210 includes a fluid container 230 and a mesh 240 overlying fluid container 230. Fluid container 230 may be supported on and/or within housing 202. A fluid "F" (e.g., water, saline, etc.) suitable to hydrate hydrogel 120a of electrode pads 120 is contained in fluid container 230. Mesh 240 may be supported on housing 202 and/or fluid container 230 such that mesh 240 is disposed in fluid communication with fluid "F" to enable the hydration of hydrogel 120a over a predetermined time period, when electrode pads 120 are supported on mesh 240, to prolong the effectiveness of hydrogel 120a. In particular, fluid "F" from container 230, hydrates hydrogel 120a of electrode pads 120.

In an embodiment, mesh 240 may include a plurality of micro pores 242 to facilitate hydration of hydrogel 120a. It is contemplated that mesh 240 may include an fluid permeable material and may be selected such that a predetermined rate of fluid transfer is obtained therethrough that is sufficient to maintain hydrogel 120a at least substantially hydrated.

As appreciated, after a predetermined time period, fluid "F" will diminish (see FIG. 3) as fluid "F" hydrates hydrogel 120a. In this regard, a refill conduit 250 may be disposed in fluid communication with fluid container 230 to enable one to refill and/or re-change fluid container 230 with fluid "F."

Figure 4:
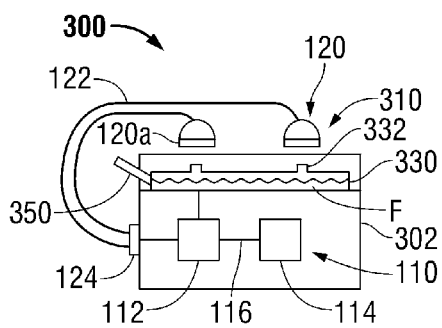
FIG. 4 is a side, elevational schematic view of an automated external defibrillator shown in a first condition according to another embodiment of the present disclosure.
Figure 5:
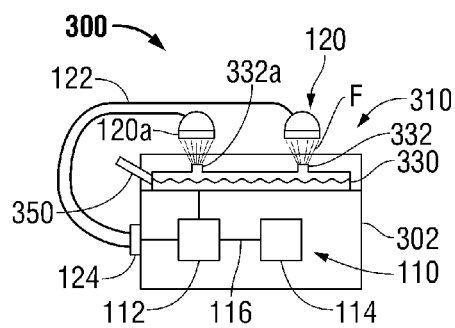
FIG. 5 is a side, elevational schematic view of the automated external defibrillator illustrated in FIG. 4 shown in a second condition.

Turning now to FIGS. 4-5, an automated external defibrillator according to another embodiment of the present disclosure is generally referred to as 300. Automated external defibrillator 300 is similar to automated external defibrillators 100 and 200 and is described herein only to the extent necessary to describe the differences in construction and operation thereof. Automated external defibrillator 300 includes a housing 302 that supports an electrode delivery system 110 and a hydrating system 310 for hydrating a hydrogel 120a supported on electrode pads 120 of electrode delivery system 110.

With continuing reference to FIGS. 4-5, hydrating system 310 is also configured to reduce a moisture vapor transmission rate of hydrogel 120a of electrode pads 120 without the need for special packaging of electrode pads 120. Hydrating system 310 includes a fluid container 330 and a sprayer system 332 with one or more sprayers 332a. Sprayer system 332 may be operably coupled to controller 112. Fluid container 330 may be supported on and/or within housing 302. A fluid "F", suitable to hydrate hydrogel 120a of electrode pads 120, is supported in fluid container 330 and may be sprayed (see FIG. 5) via one or more sprayers 332a of sprayer system 332 directly or indirectly onto hydrogel 120a of electrode pads 120 to hydrate hydrogel 120a over a predetermined time period to prolong the effectiveness of the hydrogel 120a when electrode pads 120 are disposed adjacent sprayers 332a. In particular, sprayer system 332, may include any suitable mechanical, chemical, and or electrical component such as a motor (not shown) and/or controller that is operatively coupled to controller 112 to spray fluid "F" from sprayers 332a. Notably, sprayer system 332 may include independent components such as a controller, energy source, etc. to operate sprayer system 332 independent of electrode delivery system 110. Sprayer system 332 may be configured to continuously spray, to spray at periodic intervals, and/or to spray at random intervals. To this end, any suitable spray pattern and timing thereof is contemplated. Similar to refill conduit 250 above, a refill conduit 350 may be secured to sprayer system 332 to enable one to refill and/or change fluid "F" within fluid container 330.

Electrode pads configured for use with any of the automated external defibrillators disclosed herein are shown and described in International Patent Application Serial No. PCT/US2007/010060, filed Apr. 27, 2007 (International Publication No. WO 2007/0127266); in U.S. patent application Ser. No. 12/237,803, filed on Sep. 25, 2008 (U.S. Patent Application Publication No. 2010/0072060); and U.S. patent application Ser. No. 12/043,266, filed on Mar. 6, 2008 (U.S. Patent Application Publication No. 2009/0227857), the entire content of each of which being incorporated herein by reference.

An example of a suitable polymer which may be utilized in the electrode pads disclosed herein includes RG-73P4 hydrogel, commercially available from Tyco Healthcare Group d/b/a/ Covidien. Other suitable hydrogels include those disclosed in U.S. patent application Ser. No. 12/261,122, filed on Oct. 30, 2009 (U.S. Patent Application Publication No. 2009/0270709); and U.S. patent application Ser. No. 12/261,134, filed on Oct. 30, 2009 (U.S. Patent Application Publication No. 2009/0270710), the entire disclosures of each of which are incorporated herein by reference.

It is to be understood that the foregoing description is merely a disclosure of particular embodiments and is in no way intended to limit the scope of the disclosure. Other possible modifications will be apparent to those skilled in the art and are intended to be within the scope of the present disclosure.

What is claimed is:

1. An automated external defibrillator configured to deliver electrical pulses and/or shocks to a heart of a patient during a cardiac emergency, the defibrillator comprising:
    a housing;
    a fluid container supported by the housing and configured to maintain a fluid;
    a mesh overlying the fluid and fixedly supported by the fluid container; and
    a pair of defibrillation electrode pads removably supported by the mesh, each defibrillation electrode pad supporting a hydrogel,
    wherein the fluid hydrates the hydrogel and wherein the mesh is in fluid communication with the fluid.

2. The defibrillator according to claim 1, wherein the mesh includes a fluid permeable material.

3. The defibrillator according to claim 1, wherein the mesh defines a plurality of micro pores.

4. The defibrillator according to claim 1, wherein the fluid is water.

5. The defibrillator according to claim 1, wherein the housing includes an energy source, each defibrillation electrode pad being electrically coupled to the energy source to selectively enable the deliverance of electrical pulses and/or shocks to a patient.

6. The defibrillator according to claim 5, wherein at least one of the defibrillation electrode pads are fixedly electrically coupled to the energy source.

7. The defibrillator according to claim 5, wherein the housing further supports an electrical connector, a battery, and a high voltage circuitry, and wherein each defibrillation electrode pad is pre-connected to the electrical connector of the housing so that each defibrillation electrode pad is in electrical communication with the battery and the high voltage circuitry.

8. The defibrillator according to claim 1 further comprising a refill conduit in fluid communication with the fluid container to enable introduction of the fluid into the fluid container.

9. The defibrillator according to claim 1, wherein, after a predetermined time period, the fluid will diminish as the fluid hydrates the hydrogel.

10. An automated external defibrillator configured to deliver electrical pulses and/or shocks to a heart of a patient during a cardiac emergency, the defibrillator comprising:
    a housing supporting an electrical connector, a battery, and high voltage circuitry;
    a fluid container supported by the housing and configured to maintain a fluid;
    a mesh overlying the fluid and fixedly supported by the fluid container; and
    a pair of defibrillation electrode pads removably supported by the mesh, each defibrillation electrode pad supporting a hydrogel and being pre-connected to the electrical connector of the housing so that each defibrillation electrode pad is in electrical communication with the battery and the high voltage circuitry,
    wherein the fluid hydrates the hydrogel to prolong the effectiveness of the hydrogel and wherein the mesh is in fluid communication with the fluid.

11. The defibrillator according to claim 10, wherein the mesh includes a fluid permeable material.

12. The defibrillator according to claim 10, wherein the fluid is water.

13. The defibrillator according to claim 10 further comprising a refill conduit in fluid communication with the fluid container to enable introduction of the fluid into the fluid container.

14. The defibrillator according to claim 10, wherein the mesh defines a plurality of micro pores.

* * * * *